United States Patent
Lappe et al.

(10) Patent No.: US 6,939,997 B2
(45) Date of Patent: Sep. 6, 2005

(54) PROCESS FOR PREPARING TCD-ALCOHOL DM

(75) Inventors: Peter Lappe, Dinslaken (DE); Helmut Springer, Dinslaken (DE); Rainer Lukas, Essen (DE)

(73) Assignee: Celanese Chemicals Europe GmbH, (DE)

( * ) Notice: Subject to any disclaimer, the term of this patent is extended or adjusted under 35 U.S.C. 154(b) by 0 days.

(21) Appl. No.: 10/967,580

(22) Filed: Oct. 18, 2004

(65) Prior Publication Data

US 2005/0107644 A1 May 19, 2005

(30) Foreign Application Priority Data

Nov. 8, 2003  (DE)  ................................ 103 52 260

(51) Int. Cl.$^7$ ............................................. C07C 35/22
(52) U.S. Cl. ........................................................ 568/817
(58) Field of Search .......................................... 568/817

(56) References Cited

U.S. PATENT DOCUMENTS

| | | | |
|---|---|---|---|
| 4,319,049 A * | 3/1982 | Rogier ........................ | 568/445 |
| 6,365,782 B1 * | 4/2002 | Nakamura et al. .......... | 568/444 |

FOREIGN PATENT DOCUMENTS

| | | |
|---|---|---|
| DE | 29 28 313 | 2/1981 |
| EP | 0 026 983 A1 | 4/1981 |
| EP | 0 186 075 A2 | 7/1986 |
| EP | 0 348 832 A2 | 1/1990 |
| EP | 0 811 424 A2 | 12/1997 |

OTHER PUBLICATIONS

XP-002306410 Chem.Abstracts Serv. 1981, (2 Pages).

* cited by examiner

*Primary Examiner*—Michael L. Shippen
(74) *Attorney, Agent, or Firm*—Charles A. Muserlian

(57) ABSTRACT

A process for preparing 3(4),8(9)-dihydroxymethyltricyclo[5.2.1.0$^{2,6}$]decane by hydroformylating dicyclopentadiene with subsequent distillation wherein the hydroformylation of dicyclopentadiene is carried out in two stages, and, in a first hydroformylation stage, the reaction is effected in a heterogeneous reaction system using an aqueous solution of transition metal compounds, containing water-soluble organic phosphorus (III) compounds in complex-bound form, of group VIII of the Periodic Table to give 8(9)-formyltricyclo[5.2.1.0$^{2,6}$]dec-3-ene, and, in a second hydroformylation stage, the thus obtained 8(9)-formyltricyclo[5.2.1.0$^{2,6}$]dec-3-ene is converted, in homogeneous organic phase in the presence of transition metal compounds of group VIII of the Periodic Table of the Elements to 3(4),8(9)-bisformyltricyclo[5.2.1.0$^{2,6}$]decane.

17 Claims, No Drawings

PROCESS FOR PREPARING TCD-ALCOHOL DM

The present invention relates to a process for preparing TCD-alcohol DM {3(4),8(9)-dihydroxymethyltricyclo [5.2.1.0$^{2,6}$]decane} from dicyclopentadiene (DCP).

Dicyclopentadiene (DCP), readily available by dimerizing cyclopentadiene and also prepared on the industrial scale, can be converted to compounds having important applications, to which the tricyclodecane structure imparts particular properties. The compounds, derived from DCP, having tricyclodecane structure are frequently named differently in the literature. Based on the nomenclature for DCP derivatives, disclosed by Chemiker-Zeitung, 98, 1974, pages 70 to 76, the nomenclature building on the tricyclodecane structure, also known as TCD structure, is also used hereinbelow.

TCD-Alcohol DM {3(4),8(9)-dihydroxymethyltricyclo [5.2.1.0$^{2,6}$]decane} has great economic significance as an important intermediate for the chemical industry. The dihydric alcohol is versatile and of high industrial interest for different applications: acrylic esters or methacrylic esters of tricyclic decanols containing OH groups (DE 22 00 021), as a constituent of acrylic ester adhesives curing in the absence of oxygen, (meth)acrylic esters of tricyclic decanols containing ether groups (EP 23 686), for preparing adhesives and sealants, esters and polyesters of the tricyclodecane series (DE 934 889) which are suitable as plasticizers and high-value ester lubricants, odorant compositions (DE-B 2 307 627) and polyester varnishes resistant to acid sterilization (DE 31 34 640) in the metal coatings field. TCD-alcohol DM is obtained by hydrogenating the hydroformylation products of dicyclopentadiene, known as the TCD-aldehydes.

The preparation of aldehydes by catalytic addition of carbon monoxide and hydrogen to olefinic double bonds is known. While this reaction has previously been carried out virtually exclusively using $C_0$ as a catalyst, modern processes work with metallic rhodium or with rhodium compounds as catalysts which are used alone or with complex-forming ligands, for example organic phosphines or esters of phosphorous acid. There is unanimous agreement in the technical field that active catalysts under the reaction conditions are hydridocarbonyl compounds of rhodium which can be expressed by the formula $H[Rh(CO)_{4-x}L_x]$ where L denotes a ligand and x is 0 or an integer from 1 to 3.

A special case is the hydroformylation of dienes. While the hydroformylation of conjugated dienes under the customary conditions of the oxo process provides almost exclusively monoaldehydes, it is possible to obtain not only the mono- but also the disubstitution products from dicyclopentadiene (DCP) with its isolated double bonds. Owing to the risk of a retro-Diels-Alder reaction at the temperatures of the oxo process and the associated release of cyclopentadiene which is capable of complex formation with transition metals and can reduce the activity of the catalysts used, the hydroformylation has to proceed under special conditions. It has been found to be advantageous to replace the formerly customary cobalt catalyst with rhodium, which allows a high selectivity of the conversion to aldehydes to be achieved and allows the hydroformylation under conditions under which the extent of retro-Diels-Alder dissociation is lower. A review of the hydroformylation of dicyclopentadiene and of the further processing of the TCD-aldehydes can be found in Chemiker-Zeitung 98, 1974, 70–76. 8(9)-Formyltricyclo [5.2.1.0$^{2,6}$]dec-3-ene, also known as TCD-monenal, and 3(4),8(9)-bisformyltricyclo[5.2.1.0$^{2,6}$]decane, also known as TCD-dialdehyde, are of particular significance. Owing to their thermal ability which leads to losses in distillation, the TCD-dialdehydes are usually not isolated in pure form, but rather further processed as crude products of the hydroformylation reaction.

As a consequence of the various possible applications, TCD-alcohol DM is of high economic interest and the patent literature contains numerous references to processes for its preparation.

The U.S. Pat. No. 4,647,708 describes the hydroformylation of dicyclopentadiene using Rh as a catalyst in the presence of ion exchangers (Dowex® MWA-1) in toluene/THF as solvents. The reaction is effected at 120° C. and 27.5 MPa of $CO/H_2$ (in a ratio of 1:2) in two separate continuous autoclaves. With reference to the experimental results disclosed, it can be seen that the yield of TCD-alcohol DM falls from 85% to 65% within the 30-day experimental period. The reaction system is thus unsuitable for industrial use.

U.S. Pat. No. 4,262,147 describes the use of bimetallic Rh/Co clusters on resins such as Amberlite® IRA-68. Under the conditions employed (110° C., 11 MPa, 8 hours), a selectivity of 68% of TCD-alcohol DM is obtained in this one-stage synthesis.

A modified Co process is described in DE-C 3 008 497, where dicyclopentadiene is converted under Co/tri-n-octylphosphine catalysis at 200° C. and a synthesis gas pressure of 15 MPa. After a reaction time of 5 hours, the TCD-alcohol DM is obtained in a yield of 69%. The by-products formed are 11.7% of the TCD-monoalcohol and 14.6% of hydroxymethylcyclopentane. Owing to the high temperatures which are necessarily employed, there is retro-Diels-Alder reaction of dicyclopentadiene to cyclopentadiene and thus the formation of significant amounts of hydroxymethylcyclopentane. This process variant is therefore unsuitable for industrial application.

JP 111 00 339 discloses the performance of the hydroformylation of DCP in isopropyl/toluene using rhodium dicarbonyl acetylacetonate, tris(2,4-di-tertbutylphenyl)phosphite and triethylamine at 120° C. under 8.8 MPa of synthesis gase over 8 hours. 93% of TCD-dialdehyde is obtained and is hydrogenated in isopropanol at 110° C. and 0.78 MPa of hydrogen for 6 hours over Raney nickel to give 91% of TCD-alcohol DM. The use of the complex phosphite ligands which are difficult to prepare is diadvantageous for industrial application and also for economic reasons. In addition, the broad use of phosphite ligands is restricted by their low stability and higher hydrolysis sensitivity toward water and acid traces compared to conventional phosphine ligands, and the phosphonous acids formed during the continuous hydroformylation process impair the catalyst lifetime and have to be removed from the process in a complicated manner. Moreover, when amines are used, contamination of the TCD-alcohol DM with nitrogen-containing components is always to be expected.

EP 1 065 194 describes a low-pressure process for hydroformylating dicyclopentadiene, in which the catalyst system used is likewise Rh/Tris(2,4-di-tert-butylphenyl)phosphite. The hydroformylation is carried out at pressures of 1–15 MPa and temperatures of 80–140° C. The solvents used are inert hydrocarbons such as toluene, diisopropylbenzene or methylcyclohexane. The hydroformylation product is worked up by a multistage extraction using polyhydric alcohols, for example ethylene glycol, and the addition of tertiary amines is recommended. After the extraction, the crude oxo product is present predominantly in the alcohol phase, while small proportions of mono- and dialdehyde, and also the majority of rhodium and phosphine ligands, are in the hydrocarbon phase. It is pointed out that the extraction has to be effected in the absolute absence of oxygen. The use of extractants with addition of tertiary amines, and also the absolute necessity of the absence of oxygen complicate the industrial performance of this process and include the risk of contamination of TCD-alcohol DM with traces of amines.

The known processes for preparing TCD-alcohol DM by hydroformylating dicyclopentadiene with subsequent hydrogenation entail either the presence of specific catalyst systems which are unavailable in industry or environmentally incompatible, or enable only economically unsatisfactory selectivities and yields in the hydroformylation stage to give TCD-aldehydes. There is therefore a need for a very simple and inexpensive process for hydroformylating DCP with subsequent preparation of TCD-alcohol DM.

The invention therefore consists in a process for preparing 3(4),8(9)dihydroxymethyltricyclo[ 5.2.1.0$^{2,6}$]decane by hydroformylating dicyclopentadiene with subsequent hydrogenation. The process comprises reacting dicyclopentadiene, in a first hydroformylation stage in a heterogeneous reaction system using an aqueous solution of transition metal compounds, containing water-soluble organic phosphorus (III) compounds in complex-bound form, of group VIII of the Periodic Table of the Elements at temperatures of from 70 to 150° C. and pressures of from 0.5 to 10 MPa, with synthesis gas to give 8(9)-formyltricyclo[5.2.1.0$^{2,6}$]dec-3-ene, then separating the organic phase from the aqueous phase and subsequently converting the thus obtained 8(9) formyltricyclo[5.2.1.0 $^{2,6}$]dec-3-ene, in a second hydroformylation stage in homogeneous organic phase in the presence of transition metal compounds of group VIII of the Periodic Table of the Elements at temperatures of from 70 to 140° C. and pressures of from 5 to 35 MPa by reacting with synthesis gas, to 3(4),8(9)-bisformyltricyclo[5.2.1.0$^{2,6}$]decane and subsequently hydrogenating the thus obtained 3(4),8(9)-bisformyltricyclo[ 5.2.1.0$^{2,6}$]decane to give 3(4), 8(9)-dihydroxymethyltricyclo[ 5.2.1.0$^{2,6}$]decane.

A characteristic of the inventive process for hydroformylating dicyclopentadiene is the two-stage reaction management, the first stage working by the heterogeneous biphasic process in the presence of an aqueous catalyst solution and the reaction product of the first stage, comprising predominantly TCD-monoaldehyde and small amounts of unconverted DCP, being converted without further purification, in a second stage after addition of catalyst in a homogeneous reaction medium, to TCD-dialdehyde, which is subsequently hydrogenated to give TCD-alcohol DM. This type of reaction management results in very selective hydroformylation of the double bond present in the six-membered ring of the TCD structure in the first reaction stage to give TCD-monoaldehyde, which is frequently also referred to as TCD-monenal {8(9)formyltricyclo[ 5.2.1.0$^{2,6}$]dec-3-ene}.

It is found that, surprisingly, the reaction product of the first hydroformylation stage can be hydroformylated to the TCD-dialdehyde after removing the aqueous catalyst phase without further purification in a homogeneous organic medium after addition of catalyst, even though the organic phase comprising the product of value comprises homogeneously dissolved and analytically detectable amounts of phosphorus and sulfur dissociation and decomposition products which are known to be catalyst poisons in the oxo process.

According to "New Synthesis with Carbon Monoxide" (Edited by J. Falbe, Springer-Verlag 1980, Reactivity and Structure Concepts in Organic Chemistry, Vol. 11, page 73), numerous catalyst poisons are known in rhodium-catalyzed hydroformylation. In addition to halogen, acetylenes and carboxylic acids, reference is made in particular to sulfur. Even small amounts of these catalyst poisons bring about a drastic deactivation of the hydroformylation catalyst.

For the subsequent hydrogenation step too, the crude TCD-dialdehyde product may be used without intermediate purification steps, for example distillation or wash steps. The hydrogenation of the TCD-dialdehyde to the TCD-alcohol DM is effected by conventional processes.

This is surprising inasmuch as the influence of catalyst poisons even in the hydrogenation processes carried out over fixed bed catalysts in industry is described in numerous publications. Ullmann's Encyclopedia of Industrial Chemistry, 5th edition, 1985, Vol. A1, page 283 refers to the action of sulfur-containing catalyst poisons in heterogeneously catalyzed hydrogenation processes.

Moreover, DE-B 29 18 107 refers to a distillative purification of the unsaturated aldehyde before further processing of TCD-monenal {(8)9-formyltricyclo[5.2.1.0$^{2,6}$]dec-3-ene} to give the corresponding saturated aldehyde TCD-monal.

The teaching in DE-B 26 54 221 also refers to the use of distillatively worked-up TCD-monenal for the downstream hydrogenation step.

It has likewise been found that, surprisingly, dicyclopentadiene which has not been fully converted in the first stage can be converted to the TCD-dialdehyde in the second hydroformylation stage without formation of high-boiling by-products. From this arises the advantageous possibility of a partial DCP conversion method in the first hydroformylation stage.

However, a distillative purification of TCD-monenal from the removed organic phase of the first hydroformylation stage is not ruled out. This procedure does, though, require an additional distillation step and leads to distillation losses, even if they are only small. The selective preparation of TCD-monenal from dicyclopentadiene using an aqueous catalyst solution and the distillative purification is disclosed by EP-B1-0 186 075.

The first reaction stage of the novel process is carried out as a heterogeneous reaction in a biphasic system, a reaction which is described, for example, in DE-B-26 27 354. This process is characterized by the presence of an organic phase which comprises the olefinic starting material and the reaction product, and an aqueous phase in which the catalyst is dissolved. The catalysts used are water-soluble rhodium complexes which contain water-soluble organic phosphorus (III) compounds as ligands. Examples of water-soluble phosphorus (III) compounds which form complexes with rhodium are triarylphosphines, trialkylphosphines, mixed aliphatic-aromatic phosphines and arylated or alkylated diphosphines whose organic radicals contain sulfonic acid groups or carboxyl groups. Their preparation and use are disclosed, for example, by DE-B 26 27 354, EP-B1-0 103 810, EP-B1-0 163 234 and EP-A1-0 571 819. Further groups of suitable compounds are sulfonated or carboxylated organic phosphites, and heterocyclic compounds of trivalent phosphorus, which are disclosed, for example, by EP-A1-0 575 785 and EP-A1-0 646 588.

Suitable sulfonated arylphosphines in the process according to the invention are sulfonated triarylphosphines of the general formula (I)

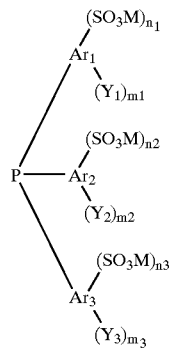

in which $Ar^1$, $Ar^2$ and $Ar^3$ are identical or different aryl groups having from 6 to 14 carbon atoms, the substituents $Y_1$, $Y_2$ and $Y_3$ are identical or different, straight-chain or branched alkyl or alkoxy radicals having from 1 to 4 carbon atoms, chlorine, bromine, the hydroxyl, cyanide or nitro group, and also the amino group of the formula $NR^1R^2$ in which the substituents $R^1$ and $R^2$ are the same or different and are each hydrogen, straight-chain or branched alkyl groups having from 1 to 4 carbon atoms, in which M is lithium, sodium, potassium, magnesium, calcium or barium, in which $m_1$, $m_2$ and $m_3$ are the same or different and are each integers from 0 to 5, in which $n_1$, $n_2$ and $n_3$ are the same or different and are each integers from 0 to 3, and at least one of the numbers $n_1$, $n_2$ and $n_3$ is equal to or greater than 1.

The triarylphosphines preferably include those triarylphosphines in which the $Ar^1$, $Ar^2$, $Ar^3$ groups are phenyl groups; $Y_1$, $Y_2$ and $Y_3$ are the methyl, the ethyl group, the methoxy, ethoxy group and/or a chlorine atom; and the cationic M radicals are inorganic cations of sodium, potassium, calcium and barium. Especially suitable are those triarylphosphines in which $Ar^1$, $Ar^2$, $Ar^3$ are each a phenyl group, $m_1$, $m_2$, $m_3$ are each 0, $n_1$, $n_2$ and $n_3$ are each 0 or 1 and $n_1+n_2+n_3$ together add up to from 1 to 3, and in which the sulfonate groups are in the meta-position.

A mixture, suitable for carrying out the hydroformylation process according to the invention, of (sulfophenyl)diphenylphosphine, di(sulfophenyl)phenylphosphine and tri(sulfophenylphosphine) is obtained in the sulfonation of triphenylphosphine, as disclosed, for example, by DE-A 26 27 354. In the prior art, (sulfophenyl)diphenylphosphine is abbreviated to TPPMS, di(sulfophenyl)phenylphosphine to TPPDS and tri(sulfophenyl)phosphine to TPPTS.

Suitable sulfonated arylphosphines are likewise sulfonated diphosphines of the general formulae (II) or (III)

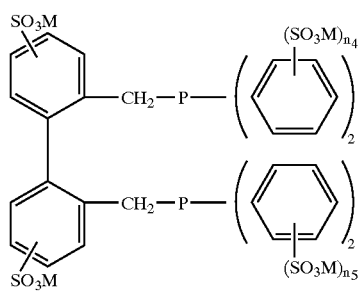

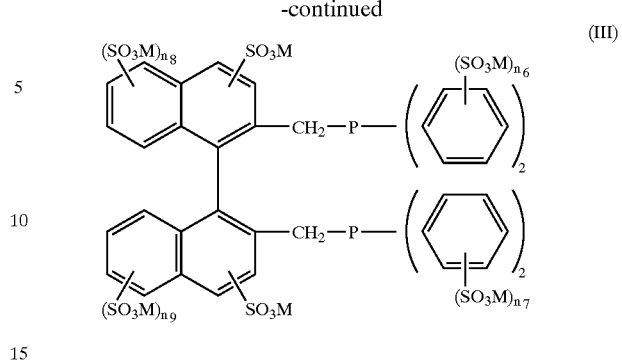

These diphosphines of the general formulae (II) and (III) are disclosed by WO 98/30526.

In (II), each $n_4$ and $n_5$ is independently 0 or 1, and the compound of the formula (II) contains up to six —$SO_3M$ groups.

In (III), each $n_6$, $n_7$, $n_8$ and $n_9$ is independently 0 or 1, and the compound of the formula (III) contains from four to eight —$SO_3M$ groups.

As a consequence of the preparation by sulfonation of the corresponding diphosphines of the formulae (IIa) and (IIa) which contain no —$SO_3M$ groups

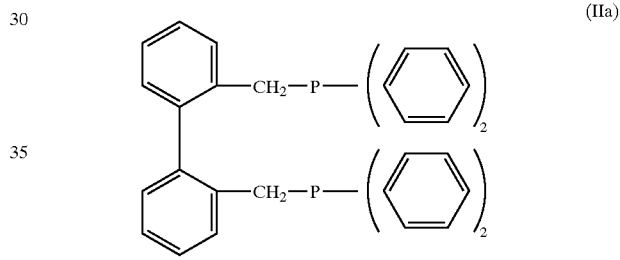

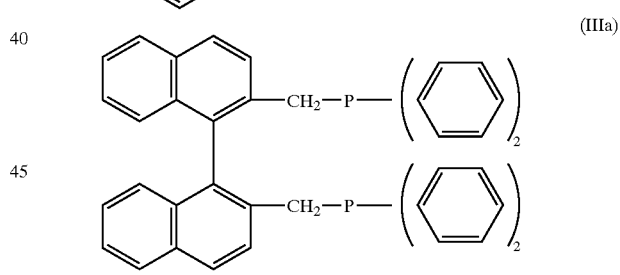

mixtures of compounds (II) and (III) with a different number of —$SO_3M$ groups are typically obtained. For instance, a compound of the formulae (II) or (III) which contains, for example, three —$SO_3M$ groups also contains compounds having only two —$SO_3M$ groups, but also compounds having four or five —$SO_3M$ groups. A compound of the formulae (II) or (III) having, for example, five —$SO_3M$ groups typically also contains compounds having only three or four —$SO_3M$ groups, but also compounds having six or seven —$SO_3M$ groups.

Compounds of the formula (II) have a maximum of six —$SO_3M$ groups, while compounds of the formula (III) have a maximum of eight —$SO_3M$ groups.

For this reason, mixtures of compounds of the formulae (II) and (III) having a different number of —$SO_3M$ groups are generally used.

In the formulae (II) and (III), M is ammonium, a monovalent metal or the equivalent of a polyvalent metal, especially sodium, potassium, calcium or barium.

It is particularly advantageous to use water-soluble complexes of rhodium, although the use of other catalytically active transition metal compounds of group VIII of the Periodic Table of the Elements is not ruled out. For instance, in the first hydroformylation stage, it is also possible to use water-soluble complexes of cobalt, iridium, nickel, palladium, platinum, iron or ruthenium, and particularly water-soluble complexes of cobalt, iridium and platinum have been found to be effective as hydroformylation catalysts.

The conditions under which the conversion in the first hydroformylation stage proceeds may vary within wide limits and be adapted to the individual circumstances. They depend, inter alia, upon the starting material, upon the catalyst system selected and upon the desired degree of conversion. Typically, the hydroformylation of the starting materials is carried out at temperatures of from 70 to 150° C. Preference is given to maintaining temperatures of from 100 to 150° C. and especially from 110 to 140° C. The overall pressure extends over a range of from 0.5 to 10 MPa, preferably from 1 to 6 MPa and especially from 1.5 to 5 MPa. The molar ratio of hydrogen to carbon monoxide varies typically between 1:10 and 10:1; mixtures which contain hydrogen and carbon monoxide in a molar ratio of from 3:1 to 1:3, especially about 1:1, are particularly suitable.

The rhodium concentration is from 20 to 1000 ppm by weight, preferably from 50 to 800 ppm by weight and especially from 100 to 600 ppm by weight, based in each case on the aqueous catalyst solution. Although it is possible to use the rhodium-phosphorus complex having stoichiometric composition as the catalyst, it is customary to work in the presence of excess phosphorus ligand, i.e. ligand which has not entered into complexation with rhodium. Per mole of rhodium, preference is given to using from 10 to 300 mol of phosphorus in the form of a water-soluble organic phosphorus compound. Particularly favorable molar ratios of rhodium to phosphorus have been found to be in the range from 1:50 to 1:150. The rhodium-phosphorus complex catalyst does not need to have a uniform composition, but rather may consist, for example, of a mixture of rhodium complexes which differ by the type of the phosphorus ligands. Equally, the free phosphorus ligand present in the aqueous catalyst solution may be composed of a mixture of different water-soluble organic phosphorus compounds.

When the catalytically active metal used is another transition metal of group VIII of the Periodic Table of the Elements, the concentration of transition metal and the molar ratio of transition metal to phosphorus vary within the ranges which are selected in the case of rhodium. The optimal values in each case can be determined by simple routine experiments as a function of the particular transition metal used.

The catalyst is typically formed from the components of transition metal or transition metal compound, organic phosphorus compound and synthesis gas under the conditions of the hydroformylation reaction in the reaction mixture. However, it is also possible to initially preform the catalyst and subsequently feed it to the actual hydroformylation stage. The conditions of the preformation generally corresponds to the hydroformylation conditions.

Dicyclopentadiene may be fed to the hydroformylation as such or in solution. Suitable solvents are water-insoluble ketones, dialkyl ethers, aliphatic nitriles, aromatic hydrocarbons such as benzene or toluene and saturated cycloaliphatic hydrocarbons such as cyclopentane or cyclohexane, or saturated aliphatic hydrocarbons.

In order to increase the conversion per unit time of dicyclopentadiene which only has low solubility in the aqueous catalyst solution, it may be advisable to add to this solution a phase transfer reagent (solubilizer). It changes the physical properties of the interfaces between the two liquid phases and eases the transfer of the organic reactants into the aqueous catalyst solution.

Solubilizers refer to compounds whose hydrophilic groups are ionic (anionic or cationic) or nonionic. The anion-active compounds include sodium, potassium or ammonium salts of carboxylic acids, preferably those having from 8 to 20 carbon atoms and especially of saturated fatty acids having from 12 to 18 carbon atoms, and also alkyl sulfates, alkylbenzenesulfonates and alkylbenzene phosphates. Examples of cationic solubilizers are tetraalkylammonium and N-alkylpyridinium salts. The nonionic phase transfer reagents do not dissociate into ions in aqueous solution. They include alkylpolyethylene glycols, alkylphenylpolyethylene glycols, fatty acid alkylolamines and trialkylamine oxides. In addition, ampholytes such as amino carboxylic acids, betaines and sulfobetaine are in use as solubilizers. Corresponding processes are disclosed, for example, by EP-B1-0 157 316.

It is also possible to use rhodium complexes which are simultaneously catalyst and phase transfer reagent. Such a procedure is, for example, the subject matter of EP-B1-0 163 234.

Also with regard to the process technology and apparatus configuration of the first stage of the novel process, it is possible to vary within wide limits. A proven embodiment of the heterogeneous hydroformylation using an aqueous catalyst phase is described in EP-B1-0 103 810. The reaction effluent of the first hydroformylation stage is separated in a phase separator into the organic product phase and into the aqueous catalyst solution. It has been found to be appropriate to circulate the catalyst solution. The crude organic product phase is fed to the second hydroformylation stage without further purification steps. However, an intermediate distillative purification of the reaction product of the first hydroformylation stage may optionally also be carried out.

The second hydroformylation stage of the novel process is carried out in a homogeneous reaction system. The term homogeneous reaction system represents a homogeneous solution composed substantially of solvent, if added in the first stage and/or in the second reaction stage, catalyst, unconverted dicyclopentadiene and TCD-monenal. In some cases, an addition of solvent in the second reaction stage may be found to be appropriate. The solvents used are organic compounds in which starting material, reaction product and catalyst system are soluble. Examples of such compounds are aromatic hydrocarbons such as benzene and toluene or the isomeric xylenes and mesitylene. Other customary solvents are paraffin oil, cyclohexane, n-hexane, n-heptane or n-octane, ethers such as tetrahydrofuran, ketones or Texanol® from Eastman. The proportion of the solvent in the reaction medium may be varied over a wide range and is typically between 10 and 80% by weight, preferably from 20 to 50% by weight, based on the reaction mixture.

However, an addition of solvent in the second, just like in the first hydroformylation stage, is not necessarily required.

The catalysts used in the second hydroformylation stage are transition metal compounds of group VII of the Periodic Table of the Elements, preferably compounds of cobalt, rhodium, iridium, nickel, iron, platinum, palladium or ruthenium and especially of cobalt, rhodium and iridium. Particular preference is given to using rhodium. The rhodium compounds used are generally not modified with phosphorus ligands such as phosphines or phosphites. Those rhodium catalysts not modified with phosphines or phosphites and their suitability as a catalyst for hydroformylation are disclosed by the literature and they are referred to as unmodified rhodium catalysts. The technical literature assumes that the rhodium compound $HRh(CO)_4$ is the catalytically active rhodium species in the hydroformylation with unmodified rhodium catalysts, even though this has not been proved unambiguously as a consequence of the many chemisms proceeding in parallel in the hydroformylation zone. Since the use of rhodium catalysts not modified with phosphines generally entails a relatively low rhodium content, preference is given to working in the second hydroformylation stage with unmodified rhodium catalysts. The rhodium content is generally from 5 to 100 ppm, based on the homogeneous reaction mixture.

However, it is also possible in the second hydroformylation stage to use rhodium complexes which contain organic phosphorus (III) compounds as ligands. Such complexes and their preparation are known (for example from U.S. Pat. No. 3,527,809, U.S. Pat. No. 4,148,830, U.S. Pat. No. 4,247,486, U.S. Pat. No. 4,283,562). They may be used as single complexes or else as a mixture of different complexes. The rhodium concentration in the reaction medium extends over a range of from about 5 to about 1000 ppm by weight and is preferably from 10 to 700 ppm by weight. In particular, rhodium is used in concentrations of from 20 to 500 ppm by weight, based in each case on the homogeneous reaction mixture. The catalysts used may be the rhodium complex having a stoichiometric composition. However, it has been found to be appropriate to carry out the hydroformylation in the presence of a catalyst system composed of rhodium-phosphorus complex and free, i.e. excess, phosphorus ligands, which no longer enters into complexation with rhodium. The free phosphorus ligand may be the same as in the rhodium complex, but it may also be possible to use ligands different therefrom. The free ligand may be a single compound or consist of a mixture of different organophosphorus compounds. Examples of rhodium-phosphorus complexes which may find use as catalysts are described in U.S. Pat. No. 3,527,809. The preferred ligands in the rhodium complex catalysts include, for example, triarylphosphines such as triphenylphosphine, trialkylphosphines such as tri(n-octyl)phosphine, trilaurylphosphine, tri(cyclohexyl)phosphine, alkylphenylphosphines, cycloalkylphenylphosphines and organic diphosphites. Owing to its ease of obtainability, triphenylphosphine is employed particularly frequently.

When operation is effected with a modified rhodium complex catalyst system, the molar ratio of rhodium to phosphorus in the homogeneous reaction mixture is typically from 1:5 to 1:200, but the molar proportion of phosphorus in the form of organic phosphorus compounds may also be higher. Preference is given to using rhodium and organically bonded phosphorus in molar ratios of from 1:10 to 1:100.

When a transition metal of group VIII of the Periodic Table of the Elements other than rhodium is used in the second hydroformylation stage, the concentration of transition metal and the molar ratio of transition metal to phosphorus, if operation is effected by the phosphine-modified process, is within the ranges which are also selected in the case of rhodium. The optimal values in each case can be determined by simple routine experiments as a function of the transition metal used in each case.

The conditions under which the reaction in the second hydroformylation stage proceeds may vary within wide limits and be adapted to the individual circumstances. They depend, inter alia, upon the starting material, upon the catalyst system selected and upon the desired degree of conversion. Typically, the second hydroformylation stage of the crude TCD-monenal is carried out at temperatures of from 70 to 140° C. Preference is given to maintaining temperatures of from 80 to 130° C. and especially from 90 to 120° C. The total pressure extends over a range of from 5 to 35 MPa, preferably from 10 to 30 MPa and especially from 20 to 30 MPa. The molar ratio of hydrogen to carbon monoxide varies typically between 1:10 and 10:1; mixtures which contain hydrogen and carbon monoxide in a molar ratio of from 3:1 to 1:3, especially about 1:1, are particularly suitable.

The catalyst is typically formed from the components of transition metal or transition metal compound and synthesis gas under the conditions of the hydroformylation reaction in the reaction mixture, optionally in the presence of organic phosphorus (III) compounds. However, it is also possible to initially preform the catalyst and subsequently feed it to the actual hydroformylation stage. The conditions of the preformation generally correspond to the hydroformylation conditions.

To prepare the hydroformylation catalyst for the first and second reaction stage, the transition metal of group VIII of the Periodic Table of the Elements, especially rhodium, is used either in metallic form or as a compound. In the metallic form, the transition metal is used either in the form of finely divided particles or precipitated in a thin film on a support such as activated carbon, calcium carbonate, aluminium silicate, clay earth. Suitable transition metals are salts of aliphatic mono- and polycarboxylic acids, such as transition metal 2-ethylhexanoates, acetates, oxalates, propionates or malonates. In addition, salts of inorganic hydrogen and oxygen acids may be used, such as nitrates or sulfates, the different transition metal oxides or else transition metal carbonyl compounds such as $Rh_3(CO)_{12}$, $Rh_6(CO)_{16}$, $CO_2(CO)_8$, $CO_4(CO)_{16}$, $Fe(CO)_5$, $Fe_2(CO)_9$, $Ir_2(CO)_8$, $Ir_4(CO)_{12}$ or transition metal complexes, for example cyclopentadienyl-rhodium compounds, rhodium acetylacetonate, (1,5-cyclooctadienyl)cyclopentadienecobalt, (1,5-cyclooctadienyl)Fe(CO)$_3$, [(1,5-cyclooctadienyl)RhCl]$_2$ or (1,5-cyclooctadienyl)PtCl$_2$. Owing to their corrosive behavior of the halide ions, transition metal halide compounds are less useful.

Preference is given to using transition metal oxides and especially transition metal acetates and 2-ethylhexanoates. It has been found that rhodium oxide, rhodium acetate, rhodium 2-ethylhexanoate, cobalt oxide, cobalt acetate and cobalt 2-ethylhexanoate are particularly suitable.

The individual hydroformylation stages may be carried out either batchwise or continuously.

The reaction product of the second hydroformylation stage is fed to the hydrogenation stage without further purification and without catalyst removal.

The hydrogenation of the crude TCD-dialdehyde to TCD-alcohol DM is effected under generally customary reaction conditions in the presence of conventional hydrogenation catalysts. In general, the hydrogenation temperature is from 70 to 170° C. and the pressure employed from 1 to 30 MPa. Suitable hydrogenation catalysts are particularly nickel catalysts.

The catalytically active metal may be applied to a support, generally in an amount of from about 5 to about 70% by weight, preferably from about 10 to about 65% by weight and in particular from about 20 to about 60% by weight, based in each case on the total weight of the catalyst. Suitable catalyst supports are all conventional support materials, for example alumina, alumina hydrates in their various manifestations, silicon dioxide, polysilicas (silica gels) including kieselguhr, silica xerogels, magnesium oxide, zinc oxide, zirconium oxide and activated carbon. In addition to the main components, nickel and support material, the catalysts may also comprise additives in minor amounts which serve, for example, to improve their hydrogenation activity and/or their lifetime and/or their selectivity.

Such additives are known; they include, for example, the oxides of sodium, potassium, magnesium, calcium, barium, zinc, aluminum, zirconium and chromium. They are added to the catalysts generally in a total proportion of from 0.1 to 50 parts by weight, based on 100 parts by weight of nickel.

However, unsupported catalysts such as Raney nickel or Raney cobalt may also be used in the hydrogenation process.

A hydrogenation stage is carried out batchwise or continuously in the liquid phase using suspended catalysts, or in the liquid or gaseous phase using fixed bed catalysts; preference is given to the continuous procedure.

In the batchwise process, based on TCD-dialdehyde, from 1 to 10%, preferably from 2 to 6% by weight of nickel in the form of the above-described catalysts is used. In the continuous procedure, from about 0.05 to about 5.0 kg of the TCD-dialdehyde are used per liter of catalyst and hour; preference is given to from about 0.1 to 2.0 kg of TCD-dialdehyde per liter of catalyst and hour.

The hydrogenation is preferably effected using pure hydrogen. However, it is also possible to use mixtures which contain free hydrogen and additionally constituents inert under the hydrogenation conditions. In any case, care has to be taken that the hydrogenation gas is free of catalyst poisons such as sulfur compounds or carbon monoxide in harmful amounts.

Surprisingly, the phosphorus- and sulfur-containing cleavage and degradation products present in the crude TCD-alcohol DM do not have a harmful effect on the hydrogenation activity of the catalyst. The transition metal, preferably rhodium, from the unremoved hydroformylation catalyst of the second hydroformylation stage precipitates virtually fully on the hydrogenation catalyst. It can be recovered by known processes.

Crude TCD-dialdehyde may be used as such or together with a solvent or diluent, although preference is given to the former variant. When solvent or diluent is added, the selection of the solvent or diluent, which may be pure substances or else substance mixtures, is not critical as long as it is ensured that they form a homogeneous solution with the feedstock. Examples of suitable solvents or diluents are linear or cyclic ethers such as tetrahydrofuran or dioxane. The amount of the solvent of diluent used may be selected freely in accordance with the circumstances of the apparatus and process, generally, solutions are used which contain from 10 to 75% by weight of TCD-dialdehyde. It has been found to be particularly useful in the process according to the invention to use the TCD-alcohol DM formed in the hydrogenation as a solvent or diluent. In this case, based on the weight of the TCD-dialdehyde, it is appropriate to add from 1 to 30 times, preferably from 5 to 20 times and in particular from 5 to 10 times, the amount of TCD-alcohol DM as a solvent and diluent.

The pure TCD-alcohol DM is recovered by conventional distillation processes. TCD-alcohol DM is drawn off as the top product. Residual amounts of the transition metal used in the second hydroformylation stage are obtained in the distillation residue and are recovered by known processes.

The process according to the invention is illustrated in detail hereinbelow with reference to some examples, but it is not restricted to the embodiments described.

EXAMPLES

The abbreviations used in the analytical characterization of the reaction products are defined as follows:

| | |
|---|---|
| DCP | dicyclopentadiene |
| TCD-monenal | 8(9)-formyltricyclo[5.2.1.0$^{2,6}$]dec-3-ene |
| TCD-dial | 3(4),8(9)-bisformyltricyclo[5.2.1.0$^{2,6}$]decane |
| Tri-CP | tricyclopentadiene |
| TPPTS means | sodium triphenylphosphinetrisulfonate |

Preparation of TCD-Alcohol DM

1. Preparation of TCD-monenal

A 5 l autoclave is initially charged with 2,119 g of TPPTS solution having a P(III) content of 472 mmol/kg which are admixed with 160.2 g of Rh solution (Rh content: 6,423 mg/kg). Afterward, a mixture of 661.1 g of dicyclopentadiene (technical grade, DCP content: 93.72% by weight) and 283.0 g of toluene is added. The reaction mixture is heated to 135° C. and converted at a synthesis gas pressure of 2.5 MPa and a reaction time of 6 hours.

After the end of the reaction, the mixture is cooled and the other, organic phase is removed from the aqueous catalyst phase by phase separation. The remaining catalyst phase is again admixed with a mixture of dicyclopentadiene and toluene and again converted. This procedure is repeated a total of eight times.

The organic phases (sum: 9,923 g) are combined and analyzed by gas chromatography.

| GC analysis (in area %) | |
|---|---|
| First runnings components | 0.32 |
| Toluene | 29.45 |
| DCP | 4.55 |
| TCD-monenal | 61.30 |
| TCD-dial | 0.81 |
| Tri-CP | 0.42 |
| Others | 3.15 |

2. Preparation of TCD-Dialdehyde 400 g of crude TCD-monenal from the first reaction stage, without employing further purification steps, are adjusted to a rhodium content of 20 ppm based on the entire reaction solution by adding a toluenic solution of rhodium 2-ethylhexanoate, and initially charged in a 1 l autoclave. The reaction mixture is heated to 120° C. and converted at a pressure of 26.0 MPa and a reaction time of 6 hours. After the end of the reaction, the mixture is cooled and decompressed, and the resulting reaction product (455.9 g) is analyzed by gas chromatography.

| GC analysis (in area %) | |
|---|---|
| First runnings components | 1.30 |
| Toluene | 31.70 |
| TCD-monenal | 2.32 |
| TCD-dial | 62.36 |
| Others | 2.32 |

3. Preparation of TCD-Alcohol DM

The TCD-dialdehyde obtained after the second hydroformylation stage is used in the hydrogenation without further purification. To this end, 450 g of TCD-dialdehyde from the second stage and 40 g of Ni 52/35 catalyst from Johnson-Matthey pic are initially charged in a 1 l autoclave. The reaction mixture is heated to 120° C. and reacted at a pressure of 10.0 MPa and a reaction time of 8 hours. After the end of the reaction, the mixture is cooled and decompressed, and the catalyst is filtered off. The thus obtained reaction product (456.0 g) is analyzed by gas chromatography.

| GC analysis (in area %) | |
|---|---|
| First runnings components | 1.37 |
| Toluene/methylcyclohexane | 30.20 |
| TCD-alcohol M | 2.52 |
| TCD-alcohol DM | 63.57 |
| Others | 2.34 |

For the workup, the crude hydrogenation product (450.0 g) is distilled on a Claisen head with condenser. 301.6 g of main fraction are obtained in a boiling range of 148–210° C. at a pressure of 1 hPa with the following composition:

| GC analysis (in area %) | |
|---|---|
| First runnings components | 0.15 |
| TCD-alcohol M | 3.46 |
| TCD-alcohol DM | 96.13 |
| Others | 0.26 |

The overall yield of TCD-alcohol DM over all stages is 89.3% of theory, based on dicyclopentadiene used. TCD-alcohol M means a monofunctional alcohol 8(9)-hydroxymethyltricyclo[5.2.1.0$^{2,6}$]decane.

The process according to the invention enables the preparation of TCD-alcohol DM in high yields, and allows the complicated purification of the intermediates to be dispensed with.

What is claimed is:

1. A process for preparing 3(4),8(9)-dihydroxymethyltricyclo-[5.2.1.0$^{2,6}$]decane by hydroformylating dicyclopentadiene with subsequent hydrogenation, comprising reacting dicyclopentadiene, in a first hydroformylation stage in a heterogeneous reaction system using an aqueous solution of transition metal compounds, containing water-soluble organic phosphorous (III) compounds in a complex-bound form, of group VIII of the Periodic Table of the Elements at temperatures of from 70 to 150° C. and pressures of from 0.5 to 10 MPa, with synthesis gas to give 8(9)-formyltricyclo [5.2.1.0$^{2,6}$]dec-3-ene, then separating the organic phase from the aqueous phase and subsequently converting the thus obtained 8(9)-formyltricyclo[5.2.1.0$^{2,6}$]dec-3-ene, in a second hydroformylation stage in homogeneous organic phase in the presence of transition metal compounds of group VIII of the Periodic Table of the Elements at temperatures of from 70 to 140° C. and pressures of from 5 to 35 MPa by reacting with synthesis gas, to 3(4),8(9)bis-formyltricyclo[5.2.1.0$^{2,6}$]decane and subsequently hydrogenating the thus obtained 3(4),8(9)-bisformyltricyclo-[5.2.1.0$^{2,6}$]decane to give 3(4),8(9)-dihydroxymethyltricyclo[ 5.2.1.0$^{2,6}$]decane.

2. The process of claim 1, wherein 8(9)-formyltricyclo [5.2.1.0$^{2,6}$]dec-3-ene obtained in the first hydroformylation stage is distilled before use in the second hydroformylation stage.

3. The process of claim 1, wherein, in the second hydroformylation stage, the reaction is effected in the presence of organic phosphorus (III) compounds.

4. The process of claim 3, wherein the organic phosphorous (III) compounds used are selected from the group consisting of triarylphosphines, trialkylphosphines, alkylphenylphosphines, cycloalkylphenylphosphines and organic diphosphites.

5. The process of claim 1, wherein the water-soluble organic phosphorus (III) compounds used in the first hydroformylation stage are sulfonated triarylphosphines of the formula

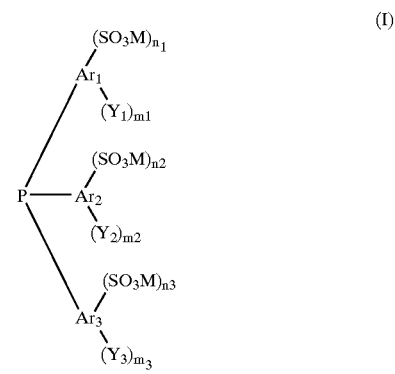

(I)

in which Ar$^1$, Ar$^2$ and Ar$^3$ are individually aryl of 6 to 14 carbon atoms, Y$_1$, Y$_2$ and Y$_3$ are individually selected from the group consisting of alkyl or alkoxy of 1 to 4 carbon atoms, chlorine, bromine, hydroxyl, cyanide, nitro, and —NR$^1$R$^2$ in which R$^1$ and R$^2$ are individually hydrogen, aralkyl of 1 to 4 carbon atoms, M is selected from the group consisting of lithium, sodium, potassium, magnesium, calcium and barium, m$_1$, m$_2$ and m$_3$ are individually integers from 0 to 5, n$_1$, n$_2$ and n$_3$ are individually integers from 0 to 3, and at least one of n$_1$, n$_2$ and n$_3$ is equal to or greater than 1.

6. The process of claim 5, wherein Ar$^1$, Ar$^2$, Ar$^3$ are each phenyl, m$_1$, m$_2$, m$_3$ are each 0, n$_1$, n$_2$, n$_3$ are each 0 or 1 and n$_1$+n$_2$+n$_3$ together add up to from 1 to 3, and the sulfonated groups are in the meta-position.

7. The process of claim 1, wherein the water-soluble organic phosphorous (III) compounds used in the first hydroformylation stage are sulfonated diphosphines of the formula

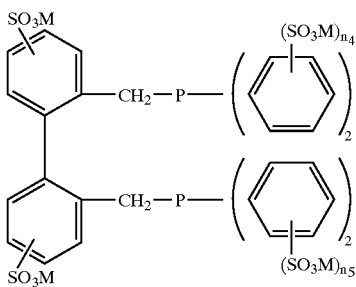

(II)

in which $n_4$ and ns are individually 0 or 1, and the sulfonated diphosphines of formula (II) contain up to six $SO_3M$ groups, and M is selected from the group consisting of ammonium, a monovalent metal and an equivalent of polyvalent metal.

8. The process of claim 1, wherein the water-soluble organic phosphorus (III) compounds used in the first hydroformylation stage are sulfonated diphosphines of the formula

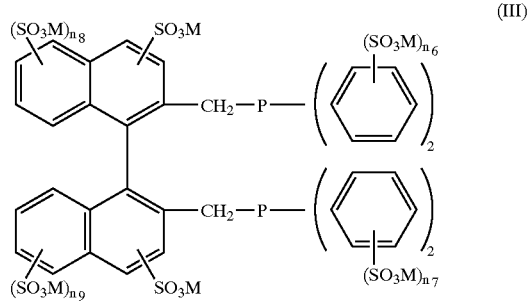

(III)

in which $n_6$, $n_7$, $n_8$ and $n_9$ are individually 0 or 1, and the sulfonated diphosphines of formula (III) contain from four to eight $SO_3M$ groups, and M is selected from the group consisting of ammonium, a monovalent metal and an equivalent of a polyvalent metal.

9. The process of claim 1, wherein the transition metal compounds, used in the first hydroformylation stage, of group VIII of the Periodic Table of the Elements are compounds of a metal selected from the group consisting of rhodium, cobalt, iridium, nickel, palladium, platinum, iron and ruthenium.

10. The process of claim 1, wherein the transition metal compounds, used in the second hydroformylation stage, of group VIII of the Periodic Table of the Elements are compounds of a metal selected from the group consisting of rhodium, cobalt, iridium, nickel, platinum, palladium, iron and ruthenium.

11. The process of claim 1, wherein the transition metal compounds, used in the first and second hydroformylation stage, of group VIII of the Periodic Table of the Elements are compounds of rhodium.

12. The process of claim 1, wherein the temperature in the first hydroformylation stage is from 100 to 150° C., and the pressure is from 1 to 6 MPa.

13. The process of claim 1, wherein the temperature in the second hydroformylation stage is from 80 to 130° C., and the pressure is from 10 to 30 MPa.

14. The process of claim 1, wherein the rhodium concentration in the first hydroformylation stage is from 20 to 1000 ppm by weight, based in each case on the aqueous catalyst solution.

15. The process of claim 1, wherein from 10 to 300 mol of phosphorus in the form of the water-soluble organic phosphorous compound are used per mole of rhodium in the first hydroformylation stage.

16. The process of claim 1, wherein the rhodium concentration in the second hydroformylation stage is from 5 to 100 ppm by weight, based on the homogeneous reaction mixture.

17. The process of claim 3, wherein the rhodium concentration in the second hydroformylation stage is from 5 to 1000 ppm by weight, based in each case on the homogeneous reaction mixture, and from 5 to 200 mol of phosphorous in the form of organic phosphorus compounds are used per mole of rhodium.

* * * * *